United States Patent
Van Overmeire et al.

(10) Patent No.: US 6,344,479 B1
(45) Date of Patent: Feb. 5, 2002

(54) METHOD OF PREVENTING RETINOPATHY OF PREMATURITY IN A NEONATE

(75) Inventors: Bart Van Overmeire, Antwerp (BE); Laszlo Darko, Westport, CT (US)

(73) Assignee: Farmacon-Il, LLC, Westport, CT (US)

( * ) Notice: Subject to any disclaimer, the term of this patent is extended or adjusted under 35 U.S.C. 154(b) by 0 days.

(21) Appl. No.: 09/813,280

(22) Filed: Mar. 20, 2001

(51) Int. Cl.$^7$ .............................................. A61K 31/24
(52) U.S. Cl. ...................... 514/534; 514/555; 514/564; 514/570; 514/912
(58) Field of Search ................................. 514/555, 533, 514/564, 534, 570, 912

(56) References Cited

U.S. PATENT DOCUMENTS

| | | |
|---|---|---|
| 4,279,926 A | 7/1981 | Bruzzese |
| 4,994,604 A | 2/1991 | Tung |
| 5,510,385 A | 4/1996 | Stroppolo |
| 5,622,990 A | 4/1997 | Katdare |
| 5,895,789 A | 4/1999 | Gentile |

*Primary Examiner*—Zohreh Fay
(74) *Attorney, Agent, or Firm*—Herbert Dubno; Jonathan Myers

(57) ABSTRACT

A method is disclosed of preventing retinopathy of prematurity in a prematurely born neonate susceptible to developing retinopathy of prematurity, which comprises the step of parenterally administering to said prematurely born neonate, a therapeutically effective amount of a water-soluble, pharmaceutically effective salt of ibuprofen as an active ingredient to promote retinal and choroidal blood flow autoregulation in said neonate.

10 Claims, No Drawings

METHOD OF PREVENTING RETINOPATHY OF PREMATURITY IN A NEONATE

FIELD OF THE INVENTION

This invention relates to a method of preventing retinopathy of prematurity in a prematurely born neonate. More particularly this invention relates to a method of preventing retinopathy of prematurity in a prematurely born neonate having a birthweight of less than 1500 grams and a gestational age at birth of less than 32 weeks.

BACKGROUND OF THE INVENTION

Retinopathy of prematurity is an eye disease which results from abnormal development of the retina, the light-sensitive lining of the eye, in prematurely born babies. The disease generally occurs in both eyes. Not all prematurely born babies develop retinopathy of prematurity, and for many the disease resolves itself without treatment in early stages. However, retinopathy of prematurity remains a common morbidity in very low birth weight infants and it can progress to a serious and potentially blinding eye problem. As the number of highest risk infants who survive increases, so does the number with retinopathy. For those babies in whom retinopathy progresses, treatment is necessary. Cryotherapy and laser treatment have some effect in advanced stages of the disease, saving a degree of vision in a proportion of the eyes that would otherwise have been blinded, but prevention awaits a better understanding of major causative factors and underlying pathophysiology.

The immature state of the retina at the time of premature delivery allows damage to the developing retinal vessels. Retinopathy occurs when abnormal blood vessels and scar tissue form at the edge of the normal retinal blood supply. The two critical areas for predicting which children are most likely to develop retinopathy are birthweight less than 1500 grams and gestational age at birth of less than 32 weeks. Other potential contributors to the disease that are currently under investigation are antenatal steroid use, alkalosis, light, chronic hypoxia, septic shock or septic episodes, and other severe physiological stresses.

If retinopathy of prematurity develops, it usually develops between 34 and 42 weeks of last conceptual age. Regressed retinopathy, whether spontaneous or after treatment, has a high incidence of sequelae such as myopia, strabismus, amblyopia, and other refractive errors. These long term vision problems correlate with abnormal fundoscopic examinations. In addition to visual difficulties, 15% of all infants with retinopathy had an adverse cosmetic outcome, including nystagmus, retrolental membrane, epiphora, corneal opacity, cataract, or episcleral hyperemia. Sometimes infants may develop glaucoma. It was also shown that neonatal retinopathy seems to be a marker for functional disability at age 5.5 years among low birth weight survivors. High rates of functional limitations in multiple domains occur in children who had retinopathy, particularly if they have unfavorable visual acuity.

It has been determined in newborn pigs that the cyclooxygenase pathway contributes to free radical formation after oxidative insults such as asphyxia, and it was demonstrated that non-steroidal anti-inflammatory drugs prevented increase in retinal malondialdehyde and hydroperoxides after asphyxia. It was also shown that indomethacin improved oxygen-induced retinopathy when administered concurrently with the injury phase without affecting the normal growth in the mouse. Nonetheless, epidemiological data suggest that postnatal administration of indomethacin to prematurely born neonates could increase the risk of developing retinopathy of prematurity (ROP).

OBJECTS OF THE INVENTION

It is the object of the invention to provide a method of preventing retinopathy of prematurity in a prematurely born infant using a non-steroidal anti-inflammatory agent that does not possess the retinopathy-promoting effects of the non-steroidal anti-inflammatory agent indomethacin.

It is a further object of the invention to provide a method of preventing retinopathy of prematurity in a prematurely born infant to promote retinal and choroidal blood flow autoregulation and to stimulate normal retinal development and retinal vascularity.

SUMMARY OF THE INVENTION

We have discovered that administration of a water-soluble, pharmaceutically effective salt of ibuprofen prevents retinopathy of prematurity when given to preterm infants, preferably during the first month of life. We have discovered a method of preventing retinopathy of prematurity in a prematurely born neonate susceptible to developing retinopathy of prematurity, which comprises the step of parenterally administering to said prematurely born neonate, a therapeutically effective amount of a water-soluble, pharmaceutically effective salt of ibuprofen as an active ingredient to promote retinal and choroidal blood flow autoregulation in said neonate.

The ibuprofen is in the form of a pharmaceutically acceptable salt of the free acid. Salts that are preferred include salts of a basic amino acid such as lysine or arginine. The basic amino acid forming the salt may be in the form of the L-isomer or in the form of the racemate. Also salts such as the methylglucamine salt are within the scope of the invention as well as pharmaceutically acceptable carboxylate-forming salts such as the alkali metal, alkaline earth metal and ammonium salts.

Administration of the water-soluble, pharmaceutically acceptable salt of ibuprofen is parenteral administration, preferably by intravenous, intramuscular or subcutaneous injection. The daily dosage of the ibuprofen salt is expressed in terms of the ibuprofen content and not in terms of the salt-forming acid administered to the prematurely born neonate is 1 to 20 mg/kg of body weight, preferably about 10 mg/kg of body weight per day. In order to have the best chance of preventing development of retinopathy of prematurity, the ibuprofen salt is preferably administered during the first month of life.

The ibuprofen salt is preferably administered to the premature neonates in 2 ml ampoules. The preferred concentration of the pharmaceutically acceptable ibuprofen salt is 1 to 20 mg, preferably 10 mg per ml of sterile aqueous solution calculated on the basis of the ibuprofen content only and not on the basis of the salt forming moiety as well.

A preferred course of administration of the ibuprofen or pharmaceutically effective salt thereof to a prematurely born neonate in need of such a treatment is carried out over three days. In the first day of treatment 10 mg of the ibuprofen salt in terms of the ibuprofen content are parenterally administered to the neonate per kg of body weight. One day later a second dose of the ibuprofen salt is administered, but the second dose is only 5 mg per kg of body weight. One day later still a third dose of the ibuprofen salt is administered, and the third dose is also 5 mg per kg of body weight. This course of administration may be repeated one or more times during the first month of life.

A typical composition for parenteral administration includes a vial or ampoule holding 20 mg of ibuprofen salt. The composition includes 20 mg of ibuprofen dissolved in 2 ml of distilled water. The composition may further include an excipient such as mannitol.

Clinical Study

A clinical study was carried out at the Neonatology Unit of University Hospital, Antwerp, Belgium. In that study the role of indomethacin and of ibuprofen was determined as a risk factor for a premature neonate's developing ROP. All of the premature neonates had a low birth of approximately between 500 to 1900 grams.

Patients and Methods: 229 prematurely born infants were included in the study. All infants were born after a gestation period of no more than 31 weeks and all infants survived for a period of at least 21 days. Prospective serial retinal observation were performed by pediatric ophthalmologist starting at a postmenstrual age of 33 weeks. Evaluation for ROP in both eyes included staging and extension of disease, zone of involvement, number of clock hours, and the presence of any additional disease. The influence of the following ante- and perinatal risk factors was assessed by uni- and multivariate analysis: tocolysis, antenatal indomethacin, and steroids, intrauterine growth restriction, twinning, gender, days on supplemental oxygen, and on ventilation, surfactant use, therapeutic indomethacin and/or ibuprofen salt use, development of bronchopulmonary dysplasia, septic episodes, and length of hospitalization, with respect to the development of ROP.

There were 123 neonates born prematurely who did not receive any non-steroidal anti-inflammatory drug (NSAID), 62 neonates who were administered indomethacin i.v., 13 who were administered a series of doses i.v. of ibuprofen lysinate followed by a series of doses of indomethacin and 31 who were administered ibuprofen lysinate i.v. per se. Where indomethacin was administered per se, each administration took place over a period of 3 consecutive time periods. On the first day 0.2 mg/kg of indomethacin were administered i.v. in a 1 ml ampoule containing distilled water. Twelve hours later 0.2 mg/kg of indomethacin was administered again in a 1 ml ampoule containing distilled water and twelve hours later still an additional 0.2 mg/kg of indomethacin was administered again in a 1 ml ampoule containing distilled water.

In the case of the ibuprofen lysinate/indomethacin series of administrations, on the first day as an initial dose 10 mg of ibuprofen lysinate per kg of body weight were administered i.v. in a 10 mg/ml ampoule with distilled water and mannitol followed 24 hours later by i.v. administration of 5 mg of ibuprofen lysinate per kg of body weight in a 5 mg/ml ampoule followed 24 hours later by another i.v. administration of 5 mg of ibuprofen lysinate per kg of body weight in a 5 mg/ml ampoule.

In some cases where the infants showed evidence of open ductus arteriosus, 2 to 6 days after the last dose of ibuprofen lysinate, a second dose of medication was administered. This time 0.2 mg of indomethacin were administered i.v. per kg of body weight followed 12 hours later by an additional i.v. administration of 0.2 mg of indomethacin per kg of body weight followed 12 hours later by yet an additional i.v. administration of 0.2 mg of indomethacin per kg of body weight.

In the case of the per se ibuprofen lysinate administration on the first day 10 mg/kg of body weight were administered i.v. in a 2 ml ampoule of distilled water and mannitol. One and two days later successive i.v. administration of 5 mg ibuprofen lysinate per kg from a 2 ml ampoule with distilled water and mannitol were again carried out.

Results: Any ROP developed in 87 neonates (38%) and threshold ROP in 9 neonates (4%) of the 229 premature neonates, with significant differences between the two groups. See Tables 1 and 2. Logistic regression analysis revealed that the risk of ROP was influenced by supplemental oxygen days (OR 1.03; 95% Cl 1.02 to 1.04; P<0.001). Infants treated with ibuprofen were less likely to develop ROP than infants without this treatment (OR 0.18; Cl 0.05–0.63; P=0.007). Overall postnatal nonsteroidal anti-inflammatory drug (NSAID) exposure was not associated with an increased risk of ROP.

TABLE 1

NSAID and ROP

| ROP yes no | No NSAID | Indomethacin | Ibuprofen followed by indomethacin | Ibuprofen | Row totals |
|---|---|---|---|---|---|
| No | 78 | 32 | 6 | 26 | 142 |
| Yes | 45 | 30 | 7 | 5 | 87 |
| All groups | 123 | 62 | 13 | 31 | 229 |

Data as numbers
Ibuprofen was administered as the lysinate salt.
Indomethacin is water-soluble and was administered as free base

TABLE 2

| Variable | No NSAID | Indomethacin | Ibuprofen followed by indomethacin | Ibuprofen | All groups |
|---|---|---|---|---|---|
| Birthweight (g) | 1080 | 1044 | 989 | 1115 | 1070 |
| Gestational age (wks) | 28.3 | 27.6 | 26.9 | 28.2 | 28 |
| Ventilation days | 14 | 21 | 22 | 15 | 16 |
| Oxygen days | 45 | 58 | 60 | 51 | 50 |
| Max ROP grades (units) | 0.66 | 1 | 1.15 | 0.26 | 0.72 |

Data as means
Ibuprofen was administered as the lysinate salt.
Indomethacin is water-soluble and was administered as free base
Bart Van Overmeire - Neonatology University Hospital Antwerp Belgium The risk of a premature neonate's developing ROP was significantly reduced by the postnatal administration of ibuprofen, independently of other studied neonatal risk factors.

What is claimed is:

1. A method of preventing retinopathy of prematurity in a prematurely born neonate susceptible to developing retinopathy of prematurity, which comprises the step of parenterally administering to said prematurely born neonate, a therapeutically effective amount of a water-soluble, pharmaceutically effective salt of ibuprofen as an active ingredient to promote retinal and choroidal blood flow autoregulation and stimulate normal retinal development and retinal vascularity in said neonate.

2. The method of preventing retinopathy of prematurity defined in claim 1 wherein the water-soluble, pharmaceutically effective salt of ibuprofen is a salt of a basic amino acid.

3. The method of preventing retinopathy of prematurity defined in claim 2 wherein the ibuprofen salt of a basic amino acid is ibuprofen lysinate or ibuprofen arginate.

4. The method of preventing retinopathy of prematurity defined in claim 2 wherein the ibuprofen salt of a basic amino acid is in the form of the L-isomer.

5. The method of preventing retinopathy of prematurity defined in claim 2 wherein the ibuprofen salt of a basic amino acid is in the form of the racemate.

6. The method of preventing retinopathy of prematurity defined in claim 1 wherein the water-soluble, pharmaceutically effective salt of ibuprofen is administered by intravenous, subcutaneous or intramuscular injection.

7. The method of preventing retinopathy of prematurity defined in claim 6 wherein the water-soluble, pharmaceutically effective salt of ibuprofen is administered in a daily dosage of 1 to 20 mg based on ibuprofen content.

8. The method of preventing retinopathy of prematurity defined in claim 6 wherein the water-soluble, pharmaceutically effective salt of ibuprofen is administered in a concentration of 1 to 20 mg/ml in a vehicle acceptable for injection.

9. The method of preventing retinopathy of prematurity defined in claim 1 wherein the water-soluble, pharmaceutically effective salt of ibuprofen is administered to the prematurely born neonate during the first month of life.

10. The method of preventing retinopathy of prematurity defined in claim 6 wherein the water-soluble, pharmaceutically effective salt of ibuprofen is administered once a day for 3 days in respective daily doses of about 10 mg, 5 mg and 5 mg per kg of body weight and the administration may be repeated.

* * * * *